United States Patent [19]
Fucci

[11] Patent Number: 5,286,253
[45] Date of Patent: Feb. 15, 1994

[54] ANGLED ROTATING SURGICAL INSTRUMENT

[75] Inventor: Joseph Fucci, Port Richey, Fla.

[73] Assignee: Linvatec Corporation, Largo, Fla.

[21] Appl. No.: 958,830

[22] Filed: Oct. 9, 1992

[51] Int. Cl.[5] .............................................. A61B 17/22
[52] U.S. Cl. ...................................... 604/22; 606/170; 606/180
[58] Field of Search ................... 604/22, 280; 606/79, 606/167, 170, 171, 180

[56] References Cited

U.S. PATENT DOCUMENTS

| | | | |
|---|---|---|---|
| 4,071,029 | 1/1978 | Richmond et al. | 606/180 |
| 4,576,772 | 3/1986 | Carpenter | 604/280 |
| 4,646,738 | 3/1987 | Trott | 606/79 |
| 4,998,527 | 3/1991 | Meyer | 604/22 |
| 5,152,744 | 10/1992 | Krause et al. | 604/22 |

*Primary Examiner*—C. Fred Rosenbaum
*Assistant Examiner*—Michael Rafa

[57] ABSTRACT

A thin-walled sleeve of polymeric or similar material is heat shrunk or otherwise closely fitted over a flexible torque-transmitting shaft in an angled rotary surgical instrument. The sheath primarily provides a seal to maintain aspiration or suction through the porous flexible shaft, and also provides an additional bearing surface on the distal end of the flexible shaft, facilitates insertion and removal of the flexible shaft, and provides a low friction surface between the flexible shaft and outer sheath of the instrument.

20 Claims, 1 Drawing Sheet

ANGLED ROTATING SURGICAL INSTRUMENT

BACKGROUND OF THE INVENTION

1. Field of the Invention

This invention relates to an improved angled rotating surgical instrument. More particularly, this invention relates to an angled rotating surgical instrument wherein suction or aspiration may be effectively applied to the surgical site.

2. Discussion of the Prior Art

U.S. Pat. No. 4,646,738 to Trott, assigned to the assignee of the present application, shows a rotary surgical tool wherein a surgical cutter is mounted for rotation at the end of an angled, elongated rigid sheath. The cutter is driven by a flexible torque-transmitting member rotating within the sheath. A proximal end of the sheath is mounted to a housing of a motor, typically disposed in a handpiece. The motor is coupled to the torque-transmitting member to drive the rotary cutter. The sheath has a bend near its distal tip which allows the surgeon access to several different portions of the surgical site through a single incision. Such bent or angled surgical instruments are becoming increasingly popular.

In order that the torque-transmitting member can drive the cutter while extending around the bend in the sheath, the torque-transmitting member must be freely flexible. According to the Trott invention, the torque-transmitting member comprises three concentric flexible tubular spring-like members. Each of the flexible tubular members is a continuous spiral-wrapped stainless steel wire of generally flat cross-section. The central of the three concentric members is wound with the opposite hand with respect to the hand of the inner and outer members, so that upon application of torque, the assembly tends to tighten upon itself. The three concentric members are secured to one another at their ends by spot welding or a like expedient. The disclosure in the Trott patent is expressly incorporated herein in its entirety by this reference.

Another generally relevant device is shown in European Patent Application No. 445,981 of Krause et al, the disclosure in which, and in any U.S. counterpart patent, is expressly incorporated herein in its entirety by this reference. In Krause et al, a flexible torque-transmitting member for a surgical instrument having an angled probe is provided by forming a number of opposed rows of interdigitated circumferential slits extending through the wall of the tubular metallic member, or by drilling a number of offset rows of holes therethrough.

In order to remove debris from the surgical site, it is desirable to apply suction or aspiration to the proximal end of the instrument, the suction or aspiration being effectively conveyed to the surgical site by way of the lumen of the tubular torque-transmitting member. In the Trott device, the fact that the torque-transmitting member comprises three concentric spiral-wrapped members allows substantial suction or aspiration to be transmitted from the proximal end to the distal tip of the instrument. However, some leakage takes place between the substantially circumferential slits formed between the adjacent spiral-wrapped wire sections, so that improvement in the efficiency of transmission of the suction or aspiration would be desirable.

In the Krause et al device, the slits or holes in the torque-transmitting member may be filled with a silicone rubber or other pliable material to permit the necessary flexibility yet allow the suction or aspiration to be effectively conveyed to the distal tip of the instrument. Such pliant plugs tend to fall out of the slits, destroying their beneficial effect.

Other generally related subject matter is shown in U.S. Pat. No. 4,858,897 to Irifune showing a spring which might be used as a flexible tension member within a sheath in an instrument of the type shown in the Trott patent. The Irifune spring would also require protection against loss of suction as in the case of the Krause et al European patent. U.S. Pat. No. 4,576,772 to Carpenter shows a fluid-tight catheter having notches cut in its surface to facilitate bending. German OS 3,219,169 of Nagel et al apparently shows various ways in which a tubular member may be perforated or slit to impart flexibility thereto. If the Nagel et al device were used as a torque-transmitting element in a probe, suction or aspiration applied to one end thereof would not be effectively transmitted to the other end.

OBJECTS AND SUMMARY OF THE INVENTION

It is accordingly an object of the invention to provide an improved angled rotating surgical instrument wherein suction or aspiration applied to a proximal end of the instrument is effectively communicated to the distal end thereof.

It is a further object of the invention to reduce friction between the torque-transmitting member and the rigid outer sheath of an angled rotating surgical instrument, to ease assembly and disassembly of the instrument for cleaning, to provide vibration absorption, and to eliminate any necessity for forming a costly, low-friction coating on the inner surface of the sheath.

These and other objects of the invention which will appear as the discussion below proceeds are satisfied by the present invention, whereby a thin sleeve of a fluid-impermeable material is placed over the flexible torque-transmitting member rotating within the sheath. Typically, the sleeve is of a so-called heat-shrink polyester material as used for electrical insulation and other such purposes; however, other materials suitable for performing the functions described herein may be employed. The sleeve is placed over the torque-transmitting member and, if made from heat-shrink polymer, is heated, whereupon the sleeve shrinks into place and is retained on the torque-transmitting member. The fluid-impermeable sleeve material has low surface friction and acts as an effective lubricant between the torque-transmitting member and the outer rigid sheath. The presence of the continuous sleeve over the flexible section of the torque-transmitting member effectively seals the torque-transmitting member, such that suction or aspiration applied to the proximal end of the instrument is effectively transmitted to the surgical site.

Other objects and advantages of the present invention will become apparent from the following description of the preferred embodiment, taken in conjunction with the accompanying drawings wherein like parts in each of the several figures are identified by the same reference characters.

DESCRIPTION OF THE PREFERRED EMBODIMENTS

Figures 1, 2:
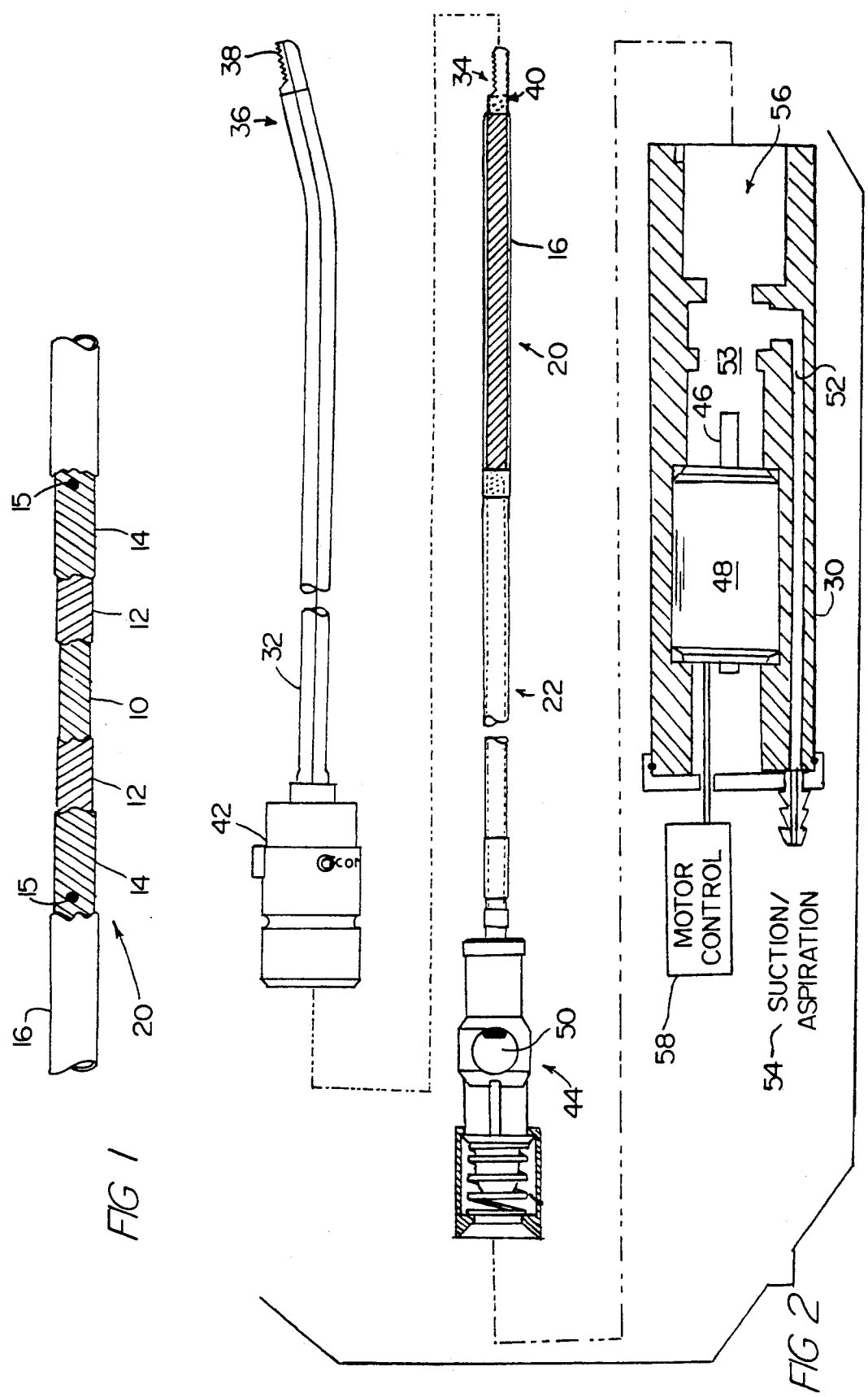
FIG. 1 shows a partial broken cut away view of the flexible section of the torque-transmitting member.
FIG. 2 shows an exploded broken partially sectional view of the complete instrument of the invention comprising a handpiece, a torque-transmitting member with a termination, and an outer rigid sheath with a corresponding termination.

FIG. 1 shows the flexible portion of the torque-transmitting member of the invention, including three concentric members 10, 12 and 14 as disclosed in the Trott patent. Members 10, 12 and 14 comprise spiral-wrapped stainless steel wire. The handedness of the inner and outer members 10 and 14 may be opposite to that of the intermediate member 12. As disclosed in the Trott patent, this arrangement of the concentric members ensures that application of torque to the assembly will cause the spiral wrap members to contract upon one another. To ensure proper operation the three concentric members may be secured to one another at their ends by a spot-weld or the equivalent as indicated generally at 15.

According to the present invention, the assembly of the three concentric members 10, 12 and 14 is covered with a very thin sleeve 16, preferably of a polymeric material and typically of a polyester heat shrinkable material. After fabrication of the flexible member comprising the three concentric members 10, 12 and 14, and their spot-welding to one another at 15, the polymeric sleeve 16 is assembled thereover and heat is supplied to shrink the sleeve snugly onto the assembly. In a preferred embodiment the polymeric sleeve is polyester heat shrink tubing having a wall thickness on the order of 0.00073 inches.

In other respects, the flexible section 20 of the torque-transmitting member 22 (FIG. 2) is as disclosed in the Trott patent. Each of the three concentric members 10, 12 and 14 may be formed by wrapping a flat stainless steel wire 0.125 inches wide by 0.003 inches thick around a mandrel of appropriate diameter.

As shown in FIG. 2, the complete angled rotary surgical instrument according to the invention includes a handpiece 30, a torque-transmitting member indicated generally at 22 and including a flexible section 20 detailed above in connection with FIG. 1, and a rigid tubular sheath 32. As indicated by the dot-dash lines in FIG. 2, in use the flexible torque-transmitting member 22 slides within the rigid sheath 32 such that the rotating cutter assembly 34 is supported at the distal tip 36 of the rigid sheath 32. The cutter assembly 34 ma comprise a stationary element 38 mounted on the sheath 32, and a rotating element 40 mounted on the torque-transmitting member 22 for rotation with respect to the stationary member 38. Preferably, the rigid sheath 32 and the torque-transmitting member 22 are provided with terminal members 42 and 44, respectively, as shown schematically in FIG. 2. The sheath 32 and torque-transmitting member 22 are thus adapted for quick release connection to the handpiece 30. Such connections are generally known to the art and may be implemented in a conventional fashion.

When the torque-transmitting member 22 and the sheath 32 have been assembled to the handpiece 30, termination 44 of the torque-transmitting member 22 is coupled to a shaft 46 of a drive motor 48 for rotating the torque-transmitting member 22 and the cutter assembly 34 within sheath 32. At the same time, suction or aspiration may be applied to a lumen extending the length of the torque-transmitting member 22 by way of a port 50 in termination 44 communicating with a passage 52 in the handpiece 30, to which is connected a source 54 of suction or aspiration as desired.

According to the invention, the fluid-impermeable sleeve member 16 allows suction or aspiration applied to the proximal end of the torque-transmitting member 22 to be effectively communicated to the distal end thereof. Since the torque-transmitting member comprises a number of substantially circumferential slits formed between the spiral-wrapped wire members, if the distal cutting window becomes clogged or obstructed, the condition known as "blow-by" or unrecoverable loss of suction may occur in the absence of sleeve 16.

The instrument of the invention is thus assembled for use by inserting the distal tip of the torque-transmitting member 22 into the terminal member 42 of the rigid sheath 32, and sliding the termination 42 of the sheath into recess 56 of the handpiece 30, such that the termination 44 engages an inner corresponding recess 53 in the handpiece 30, and so that motor shaft 46 engages termination 44. At that point the rotating cutter element 40 fits snugly within the stationary member 38 fixed at the distal end of the ridged sheath 32 and is supported thereby. When the motor 48 is subsequently actuated by motor control 58, the torque-transmitting member rotates, rotating cutter 40 with respect to stationary cutter 38, thereby forming an effective cutting instrument. Suction or aspiration may then be provided at 54 to withdraw or flush debris from the surgical site.

As indicated above, the provision of sleeve 16 over the flexible portion 20 of torque-transmitting member 22 provides a number of useful functions. The fluid-impermeable sleeve seals the flexible member 20 despite the presence of essentially circumferential slits formed between the flat wires of the concentric members 10, 12 and 14. Stated differently, sleeve 16 provides a seal over the discontinuous surface of flexible portion 20 of torque-transmitting member 22. Sleeve 16 further provides a low friction interface between the flexible member 20 and the interior of the rigid sheath 32. This not only eases assembly and disassembly of the instrument, but also eliminates any necessity of providing a costly low friction coating on the interior surface of the rigid sheath 32.

As noted above, the preferred embodiment of the invention utilizes heat-shrink polyester tubing for sleeve 16. It will be appreciated, however, that other materials may be employed and need not be applied by heat shrinking. It is only necessary that the resulting sleeve be capable of performing the functions ascribed thereto in the foregoing description. The most important of these functions is sealing the torque-transmitting member in order that the distal end of the cutter may be efficiently aspirated from the proximal end. In addition, the sleeve should provide the bearing and vibration damping functions described above, although these are not as critical as fluid impermeability. Of course, the sleeve also must not interfere with the rotation of the torque-transmitting member. One alternative to the heat shrink polyester material is Teflon which has all of the desirable features required for sleeve 16. A Teflon sleeve 16 would take the form of a tube journaled or "free-wheeling" about the torque-transmitting member. Still another alternative embodiment of sleeve 16 is a "spray-on" resin or other material that is sprayed as a liquid and solidifies on the torque-transmitting member.

It should also be noted that the fluid-impermeable sleeve of the present invention is useful to preclude aspiration leakage in instruments other than angled cutters. Thus, the sleeve is useful in straight cutters and in non-cutting instruments through which aspiration of a surgical site is effected. It is also useful in cutters or the like that are conformable to shape by the end user. Such a cutter may be supplied by its manufacturer without bends but is bent to a desired angle before use.

While as indicated the cooperating cutting elements may be permanently fixed to the distal ends of the tubular sheath and torque-transmitting member, it is also within the scope of the invention to provide separable cutter assemblies.

Other aspects of the construction of the complete instrument according to the invention are generally as taught in the Trott patent and need not be reiterated here. However, the invention is not limited to the particular flexible member disclosed by Trott, but is also useful in connection with the device shown in the Krause et al European patent. If the Irifune spring were employed as a flexible element in a rotating surgical instrument it would similarly be substantially improved by placement of a fluid-impermeable sleeve 20 thereover according to the invention.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An angled motor-driven rotating surgical instrument, comprising:
   a motor assembly;
   a rotating cutter assembly;
   a rigid elongated tubular sheath having a proximal end configured to be coupled to said motor assembly and a distal end including means for rotatably supporting a rotating cutter assembly, said tubular sheath having a bend formed intermediate said ends;
   a torque-transmitting member received within said sheath and comprising a flexible section juxtaposed to the bend in said sheath;
   said motor assembly including a coupling for receiving said proximal end of said sheath to apply torque to rotate said torque-transmitting member within and relative to said sheath; and
   wherein said rotating cutter assembly is engaged with the distal end of said torque-transmitting member for rotation therewith;
   wherein said flexible section of said torque-transmitting member comprises:
   a tubular inner member having a plurality of substantially circumferential slits formed therein to allow flexibility of said inner member while it is being rotated within said bend in said tubular sheath; and
   a tubular sleeve of a polymeric material secured to said inner member within said tubular sheath.

2. The instrument of claim 1, further comprising means for delivering aspiration forces to the proximal end of said sheath, and wherein said inner member has a lumen extending through its center and said tubular sleeve effectively seals said slits to communicate said aspiration forces from the proximal end of said sheath to the distal end thereof.

3. The instrument of claim 2, wherein said inner member comprises three concentric tubular members each comprising a continuous length of spiral-wrapped wire, whereby said slits are formed between adjacent sections of said wire.

4. The instrument of claim 3, wherein the wire of said concentric tubular members is flat in cross-section.

5. The instrument of claim 3, wherein the wire of said concentric tubular members is of stainless steel.

6. The instrument of claim 3, wherein said concentric tubular members are joined to one another at at least one end of said inner member.

7. The instrument of claim 6, wherein said joinder of said concentric tubular members is effected by spot-welding.

8. The instrument of claim 3, wherein the relative direction of spiral wrapping of said three tubular concentric members is arranged such that application of torque to said torque-transmitting member tends to tighten said concentric tubular members with respect to one another.

9. The instrument of claim 8, wherein the innermost and outermost of said concentric tubular members are spiral-wrapped in one circumferential direction, and the third concentric tubular member, being disposed between said innermost and outermost concentric tubular members, is spiral-wrapped in the opposite circumferential direction.

10. The instrument of claim 2, wherein said inner member is tubular and opposed rows of interdigitated circumferential slits are formed through said tubular member along its length.

11. The instrument of claim 1, wherein said tubular sleeve is formed of a heat-shrinkable polyester material.

12. An endoscopic instrument comprising:
   a rigid elongated tubular sheath having a proximal end and a distal end; and
   a shaft member disposed within said sheath, said shaft member comprising:
   a hollow tubular member for conducting aspirating fluid from said distal end to said proximal end; and
   a thin-walled sleeve of fluid-impermeable material fitted over said hollow tubular member to seal against leakage of the aspirating fluid from said tubular member;
   a drive motor unit;
   a cutter assembly;
   wherein the proximal end of said sheath is mounted on said drive motor unit;
   wherein said cutter assembly is supported at the distal end of said sheath;
   wherein said shaft member is a torque-transmitting member coupled to receive torque from said drive motor unit and to transmit the received torque to said cutter assembly; and
   wherein said sheath has a bend intermediate said proximal and distal ends, and wherein said hollow tubular member is flexible to adapt to said bend in said sheath.

13. A method of manufacture and use of an angled motor-driven rotating surgical instrument, comprising the steps of:
   attaching a proximal end of a rigid tubular sheath to a drive motor;
   supporting a rotating cutter assembly at a distal end of said tubular sheath;
   forming a bend in said tubular sheath intermediate said proximal and distal ends;
   disposing a tubular torque-transmitting member within said tubular sheath such that a flexible torque-transmitting section of the torque-transmitting member is juxtaposed to the bend in said tubular sheath;

coupling said drive motor to said torque-transmitting member to rotate said torque-transmitting member relative to and within said tubular sheath;

assembling a sleeve of a polymeric material over said flexible section of said torque-transmitting member; and whereby said torque-transmitting member with said polymeric sleeve assembled thereover is disposed within and is rotatable relative to said tubular sheath.

14. The method of claim 13, further comprising the step of forming said torque-transmitting member by assembling three concentric members, each comprising a length of spiral-wrapped wire.

15. The method of claim 14, wherein the direction of spiral wrapping of each of said three concentric members is arranged such that application of torque to said torque-transmitting member tends to tighten said concentric members with respect to one another.

16. The method of claim 15, wherein the innermost and outer-most of said concentric members are spiral-wrapped in one circumferential direction, and the third of said concentric members, being disposed between said innermost and outermost of said concentric members, is spiral-wrapped with the opposite hand.

17. The method of claim 16, wherein said concentric members are stainless steel, and comprising the further step of fixing said concentric tubular members to one another at at least one end thereof by welding.

18. The method of claim 13, wherein said polymeric sleeve is of a heat shrinkable polyester material, and comprising the further step of applying heat thereto to fix said sleeve over said flexible section of said torque-transmitting member.

19. The method of claim 13, wherein said torque-transmitting member is fabricated by forming rows of opposed interdigitated circumferential slits in a tubular member, whereby said tubular member is rendered substantially flexible.

20. The method of claim 13, comprising the further step of applying aspiration or suction to a proximal end of said tubular torque-transmitting member for communication to a surgical site.

* * * * *